ations, vol. 14, No. Special Issue, p. 583-584, Aug. 1, 2007.
United States Patent
Wilk et al.

(10) Patent No.: US 9,310,386 B2
(45) Date of Patent: Apr. 12, 2016

(54) IN VITRO ASSAY FOR QUANTIFYING CLOSTRIDIAL NEUROTOXIN ACTIVITY

(75) Inventors: Thomas Wilk, Limburgerhof (DE); Harold Victor Taylor, Frankfurt am Main (DE); Karl-Heinz Eisele, Frankfurt am Main (DE)

(73) Assignee: MERZ PHARMA GmbH & CO. KGaA, Frankfurt am Main (DE)

( * ) Notice: Subject to any disclaimer, the term of this patent is extended or adjusted under 35 U.S.C. 154(b) by 160 days.

(21) Appl. No.: 13/574,113

(22) PCT Filed: Jan. 19, 2011

(86) PCT No.: PCT/EP2011/000204
§ 371 (c)(1),
(2), (4) Date: Oct. 12, 2012

(87) PCT Pub. No.: WO2011/088993
PCT Pub. Date: Jul. 28, 2011

(65) Prior Publication Data
US 2013/0022992 A1        Jan. 24, 2013

Related U.S. Application Data

(60) Provisional application No. 61/336,502, filed on Jan. 22, 2010.

(30) Foreign Application Priority Data

Jan. 22, 2010   (EP) .................................... 10000667

(51) Int. Cl.
| | | |
|---|---|---|
| *C12Q 1/06* | (2006.01) | |
| *C12Q 3/00* | (2006.01) | |
| *C12N 13/00* | (2006.01) | |
| *G01N 33/531* | (2006.01) | |
| *G01N 33/94* | (2006.01) | |
| *C12Q 1/37* | (2006.01) | |

(52) U.S. Cl.
CPC ........ *G01N 33/94* (2013.01); *C12Q 1/37* (2013.01); *G01N 2333/33* (2013.01)

(58) Field of Classification Search
CPC .......... A61K 38/4893; G01N 2333/00; G01N 2333/33; G01N 2333/195; G01N 2405/00; G01N 2469/00
See application file for complete search history.

(56) References Cited

U.S. PATENT DOCUMENTS 6,504,006 B1    1/2003   Shine et al.

OTHER PUBLICATIONS

Bagramyan et al., (PLoS ONE 2008. vol. 3(4): e204:pp. 1-9. Published Apr. 30,008).*
Singh et al., (Anal. Chem. 2000. vol. 72:6019-24).*
Montecucco et al., (Biochem J. 1989.vol. 259(1):47-53).*
Evans, E.R., et al., Journal of Applied Microviology, vol. 107, No. 4, p. 1384-1391, Oct. 2009.
Fu Fen-Ni, et al., Journal of Protein Chemistry, NOL. 18, No. 6, p. 701-707, Aug. 6, 1999.
International Search Report With Written Opinion for PCT/EP2011/000204 of Feb. 15, 2011.
Pearce L. Bruce, et al., Toxicon, vol. 35, No. 9, p. 1401-1403, Sep. 1, 1997.
Petr Capek & Tobin Dickerson, Toxins, vol. 2, No. 1, p. 24-53, Jan. 7, 2010.
Sesardic, D., et al., AATEX—Alternatives to Animal Testing and Experimentation, vol. 14, No. Special Issue, p. 583-584, Aug. 1, 2007.
Singh, A.K., et al., Analytical Chemistry, vol. 72, No. 24, p. 6021-6023, Dec. 15, 2000.
Sweta Parikh, et al., Journal of Protein Chemistry, vol. 26, No. 1, p. 21-25, Jan. 10, 2007.
Rummel, et al. Identification of the protein receptor binding site of botulinum nerutoxins B and G proves the double-receptor concept. PNAS vol. 104(1), pp. 359-364, 2007.

\* cited by examiner

*Primary Examiner* — J. Hines
(74) *Attorney, Agent, or Firm* — Hueschen and Sage

(57) ABSTRACT

Novel methods for determining the unknown biological activity of a clostridial neurotoxin in a sample with respect to the known biological activity of a clostridial neurotoxin in a reference sample, comprising the step of comparing the biological activity of a clostridial neurotoxin preparation with the biological activity of a standard preparation of a reference clostridial neurotoxin in certain in vitro systems.

14 Claims, No Drawings

IN VITRO ASSAY FOR QUANTIFYING CLOSTRIDIAL NEUROTOXIN ACTIVITY

FIELD OF THE INVENTION

This invention relates to novel methods for determining the unknown biological activity of a clostridial neurotoxin in a sample with respect to the known biological activity of a clostridial neurotoxin in a reference sample. The method comprises the step of comparing the biological activity of a clostridial neurotoxin preparation with the biological activity of a standard preparation of a reference clostridial neurotoxin in certain in vitro systems.

BACKGROUND OF THE INVENTION

In recent years, botulinum neurotoxins have become the standard agent in the treatment of focal dystonias and spastic indications. Treatment of patients generally involves injection of the neurotoxin into affected muscle tissue, bringing the agent near the neuromuscular end plate, i.e. close to the cellular receptor mediating its uptake into the nerve cell controlling said affected muscle. Various degrees of neurotoxin spread have been observed. This spread is thought to correlate with the injected amounts and the particular preparation of neurotoxin injected. Resulting from the spread, systematic side effects caused by the inhibition of acetylcholine release, may be observed at nearby muscle tissue. The incidents of unintended paralysis of untreated muscles can largely be avoided by reducing the injected doses to the therapeutically relevant level. Overdosing may also be a problem with regard to the patients' immune system, as the injected neurotoxin may trigger the formation of neutralizing antibodies. If this occurs, the neurotoxin will be inactivated without being able to relieve the involuntary muscle activity.

Differences in the dose equivalents or variations in the determined activity of preparations such as available sales products or batches produced during the manufacturing process, commonly a fermentation process, pose an increased risk for patients through possible side effects and the development of immunity. Therefore, it is of crucial importance to determine the biological activity of a clostridial neurotoxin contained in said sales products or production batches reliably (i.e. without significant variation) and as accurately as possible, in order to adjust the neurotoxin concentration to a reliable effective dose for the benefit of the patient. This may also serve as an incentive to the manufacturers to offer formulations allowing optimum exploitation of biological activity for different therapeutic purposes.

At present, the botulinum neurotoxin testing is predominantly performed using the mouse $LD_{50}$ assay developed more than 40 year ago (see Boroff and Fleck, J. Bacteriol. 92 (1966) 1580-1581), which is accepted for potency testing by United States and European regulatory agencies. This assay involves dosing mice with dilutions of the sample of botulinum neurotoxin being tested and calculating the dilution at which 50% of the mice would be expected to die. Since this bioassay requires up to 100 mice for testing a single sample, and takes up to four days to generate results, there is a large need for alternative methods that are faster and more accurate, and/or reduce, cause less pain, distress, and/or replace use of animals such as mice. Any such alternative method, in order to be acceptable to regulatory agencies for the determination of potency, must be suitable for the intended purpose of the product in question and must be validated for sensitivity, specificity, reproducibility and robustness. For botulinum neurotoxin testing, a suitable potency assay must be used to determine the dose of the final product or to compare the relative activities of different lots. Because botulinum neurotoxin activity is dependent upon three functional domains within the protein molecule, an acceptable potency assay must account for the activity of all domains. For a discussion of issues relating to the unsolved problem of mouse $LD_{50}$ assay replacement, see "Report on the ICCVAM-NICEATM/ECVAM Scientific Workshop on Alternative Methods to Refine, Reduce or Replace the Mouse LD50 Assay for Botulinum neurotoxin Testing", NIH Publication Number 08-6416, February 2008.

For example, several cell-based assays using a Western Blot readout have been discussed in the context of identifying alternatives to the mouse $LD_{50}$ assay. Eubanks et al. describe an antibody-based assay for detection of SNAP25 cleavage by BoNT/A in PC12 or Neuro-2A cells (Eubanks et al., FEBS Lett. 2005; 579: 5361-4). A similar assay is based on the detection of $SNAP25_{197}$ in differentiated Neuro-2A cells (Fernandez-Salas et al., ABS-29 presented at: Basic and Therapeutic Aspects of Botulinum and Tetanus Toxins International Conference (Toxins 2005), Jun. 23-25, 2005, Denver, Colo.; Steward et al., ABS-76 presented at: Basic and Therapeutic Aspects of Botulinum and Tetanus Toxins International Conference (Toxins 2005), June 23-25, 2005, Denver, Colo.).

Alternatively, cellular assays were set up that monitor the neuronal network or neurotransmitter release on clostridial neurotoxin treatment. Chaddock et al. describe an assay based on the detection of potassium stimulated $^3$H-glycine release in a primary culture of fetal rat spinal cord cells on treatment with BoNT/A (Chaddock et al., Protein Expr Purif. 2002; 25: 219-28). Gross et al. used the reduction of spontaneous spiking and bursting as read-out in embryonic murine spinal cord and frontal cortex cells (Gross et al., Society for Neurosciences 2003, Abstract 122.9). That assay was originally developed by Keefer et al. using either BoNT/A or tetanus toxin (Keefer et al., Society for Neurosciences 2001, Abstract 1302).

Additionally, cellular assays were studied using Botulinum neurotoxin substrates carrying fluorescence markers. Dong et al. presented a FRET-assay in PC12 cells using SNAP25 or Synaptobrevin each labelled with two fluorescent proteins for monitoring BoNT/A and BoNT/B activity, respectively (Dong et al., Proc. Natl. Acad. Sci. U.S.A. 2004; 101: 14701-6). A similar assay was set up by Steward et al. in differentiated Neuro-2A cells (Steward et al., International Conference on Basic and Therapeutic Aspects of Botulinum and Tetanus Toxins, 23-25 June 2005, Denver, USA: ABS-76).

The above referenced prior art methods, however, have not resulted in a method certified by regulatory authorities. Therefore, the out-of-time mouse killing assay must still be performed, and the need still exists to identify alternative assays.

OBJECTS OF THE INVENTION

It was an object of the invention to improve the methods of the prior art and to develop reliable and accurate methods for determining the unknown biological activity of clostridial neurotoxins in a sample, particularly for pharmaceutical and/or aesthetic use, so that such methods might be used for regulatory purposes. Such an improved method would also serve to satisfy the great need for a safe and effective administration.

SUMMARY OF THE INVENTION

Surprisingly it has been found that the methods for determining the unknown concentration of botulinum neurotoxins in a sample for clinical and/or aesthetic use can be developed in in vitro systems.

In one aspect, the present invention relates to an in vitro method for determining the biological activity of a preparation of a clostridial neurotoxin, comprising the steps of:
(a) contacting at least one test particle with a sample of said preparation; and
(b) comparing the biological effect of said sample with the biological effect of a reference sample;
wherein said at least one test particle comprises at least a membrane enclosing a reaction volume, wherein said membrane carries one or more receptors for said clostridial neurotoxin capable of mediating transfer of said clostridial neurotoxin to said reaction volume, and wherein said reaction volume comprises a substrate for the proteolytic activity of said clostridial neurotoxin.

In another aspect, the present invention also relates to a kit for an in vitro method for determining the biological activity of a preparation of a clostridial neurotoxin, comprising:
(a) at least one test particle, wherein said at least one test particle comprises at least a membrane enclosing a reaction volume, wherein said membrane carries one or more receptors for said clostridial neurotoxin capable of mediating transfer of said clostridial neurotoxin to said reaction volume, and wherein said reaction volume comprises a substrate for the proteolytic activity of said clostridial neurotoxin; and
(b) one or more reagents for determining binding of said clostridial neurotoxin to said one or more receptors; and/or
(c) one or more reagents for determining proteolysis of said substrate.

DETAILED DESCRIPTION OF THE INVENTION

The present invention may be understood more readily by reference to the following detailed description of the invention and the examples included therein.

In the context of the present invention, the term "in vitro" refers to a system that is not a living organism (i.e. not "in vivo"). Furthermore, an "in vitro" system does not include a functional multi-cellular part taken from such an organism, e.g. an organ or organ preparation.

In the context of the present invention, the term "clostridial neurotoxin" refers to a natural neurotoxin obtainable from bacteria of the class Clostridia, including *Clostridium tetani* and *Clostridium botulinum*, or to a neurotoxin obtainable from alternative sources, including from recombinant expression or from genetic or chemical modification of such a natural neurotoxin. Particularly, the clostridial neurotoxins have endopeptidase activity. Said neurotoxin may be obtained from a clostridial cell or by expression of the neurotoxin in a heterologous cell such as *E. coli*.

In the context of the present invention, the term "preparation of a clostridial neurotoxin" refers to a composition comprising a clostridial neurotoxin, including, but not limited to, the raw material obtained from a fermentation process (supernatant, composition after cell lysis), a fraction comprising a clostridial neurotoxin obtained from separating the ingredients of such a raw material in a purification process, an isolated and essentially pure clostridial neurotoxin, and a formulation for pharmaceutical and/or aesthetic use comprising a clostridial neurotoxin and additionally pharmaceutically acceptable solvents and/or excipients.

The term "contacting" as used herein means exposing the test particle to the sample. One way of exposing the test particle to the sample is to incubate (bathe) the test particle in the sample. To this end, the test particle may be positioned e.g. in a reaction vessel containing a physiological buffer. The skilled person will realize that the choice of the buffer depends on the particularities of the test particle. In order to expose the test particle to the sample, a suitable amount of the sample may be added to the reaction vessel.

The skilled person will recognize that a minimal incubation period may be required to observe an effect of the sample comprising the clostridial neurotoxin on the test particle. Although incubation periods may be different from test particle to test particle, the skilled person can easily establish suitable conditions, which will also depend on the final concentration of the neurotoxin.

In the context of the present invention, the term "reference sample" refers to a sample taken from a standard preparation of a reference clostridial neurotoxin, i.e. from a preparation comprising a clostridial neurotoxin, where the biological activity of a given amount of such standard preparation is known. The biological activity of such standard preparation may, for example, be determined by the mouse $LD_{50}$ assay described above. The $LD_{50}$ value defines the quantity of neurotoxin at which 50% of a mouse population is killed if said quantity is applied to the mice of said mouse population. The $LD_{50}$ value defines the so-called "unit" that is the commonly accepted unit used to define a quantity of a clostridial neurotoxin contained in a sample. The method for determining said value is known to the person skilled in the art. The method is documented in the European Pharmacopoeia ($6^{th}$ edition; available from European Directorate for the Quality of Medicines & HealthCare (EDQM), 7 allée Kastner, CS 30026, F-67081 Strasbourg, France).

In the context of the present invention, the term "test particle" refers to a particle that is characterized by at least an outer surface enclosing at least one cavity containing a reaction volume. Typically, the outer surface of said test particle is a lipid bilayer enclosing a luminal reaction volume. The particle may be generated de novo from its components or may be obtained from a cell by preparation methods known in the art (Gray, E. G. & Whittaker, V. P. (1962) J. Anat. (London) 96, 79-87). For example, test particles suitable for the method of the present invention may be obtained in the following manner: eighteen rats are decapitated, and the brains quickly removed. The following procedures are carried out at 0-4° C. The tissue (about 25 g, wet weight) is homogenized in 9 volumes of ice-cold 0.32 M sucrose in 3 mM Hepes-NaOH buffer, pH 7.4. The homogenate is centrifuged at 1,000×g for 10 min. The supernatant is centrifuged at 10,000×g for 40 min. The pellet is suspended in 9 volumes of 0.8 M sucrose in 3 mM Hepes-NaOH buffer, pH 7.4, and centrifuged at 80,000×g for 90 min. The pellet is washed twice by centrifugation at 10,000×g for 10 min with 9 volumes of 3 mM Hepes-NaOH buffer, pH 7.0, containing 0.12 M NaCl, 2.5 mM KCl, 2 mM $MgCl_2$ and 2 mM $CaCl_2$, (HBS). The washed pellet, designated as the crude synaptosomal fraction, is disrupted in 2 volumes of 10 mM Hepes-NaOH buffer, pH 7.0, containing 1 mM EDTA (Dojindo Laboratories) and 1 mM dithiothreitol (Sigma) and then mixed with an equal volume of the same buffer containing 40 mM MEGA-9 (Dojindo). After 30 min on ice, the insoluble materials are removed by centrifugation at 80,000×g for 60 min. The supernatant is referred to as the MEGA-9 extract. In order to avoid proteolytic degradation of the protein receptor, a mixture of protease inhibitors is added to the buffer used throughout solubilization and purification. These protease inhibitors are phenylmethylsulfonyl fluoride (0.1 mM, Sigma), pepstatin A (5 pg/ml, Peptide Institute, Inc.), and calpain inhibitors I and II (3 pg/ml, Nacalai Tesque). The diameter of such test particles is typically between 10 nm and 1 mm, particularly between 0.1 and 10 μm.

In an alternative embodiment, the "test particle" is represented by a second test chamber separated from a first test chamber by a membrane, similar to the setup described in Simon & Blobel (A protein-conducting channel in the endoplasmic reticulum. Cell. 1991 May 3;65(3):371-80). In such a setting, the first test chamber corresponds to the outer reaction volume, wherein said sample of said preparation of a clostridial neurotoxin is placed. The membrane, e. g. a lipid bilayer, corresponds to the surface of said test particle, and the second test chamber corresponds to the test particles inner cavity containing the reaction volume. In the method according to this alternative embodiment, the sample is put in the first test chamber, said membrane carries one or more receptors for said clostridial neurotoxin capable of mediating transfer of said clostridial neurotoxin to said second chamber, and said second chamber comprises a substrate for the proteolytic activity of said clostridial neurotoxin.

The term "reaction volume" as used herein refers to the volume covered, and separated from the external volume, by the membrane surrounding the test particle. Within the reaction volume, the reaction between the clostridial neurotoxin comprised in the sample of the clostridial neurotoxin preparation and the reaction partners for the clostridial neurotoxin, e.g. a substrate, or other reactions resulting in an observable and/or detectable biological effect may take place. Typically, the reaction volume is at physiological pH and osmolarity under reducing conditions, e.g. by the presence of glutathione, mercaptoethanol or DTT, and optionally ATP.

The term "biological effect" as used herein refers to change or modification of the status of the test particle that can be determined either directly or indirectly be observing one or more parameters associated with such change or modification. Examples of such changes or modifications are e.g. binding events, resulting in the formation of dimeric or multimeric structures, enzymatic reactions, such as proteolytic reactions, resulting in a decrease of substrates, and an increase in products resulting from the enzymatic reaction, such as one or more cleavage products from proteolysis, or changes to the release of signaling molecules, e.g. a neurotransmitter such as acetylcholine etc., from a test particle.

According to the present invention's teaching, the biological effect of the sample containing the clostridial neurotoxin is compared to the effect of a reference sample. The term "reference sample" refers to a preparation with a known quantity of neurotoxin. In one embodiment, the effect of the sample is compared to a standard dose-response curve established by measuring the effect of several reference samples, each containing a different amount of the reference neurotoxin. In certain embodiments, the quantity of the reference sample (i.e. the amount per standard unit, e.g. mg/ml, or mg/kg of body weight) is plotted on the X axis and the response is plotted on the Y axis. Commonly, it is the logarithm of the quantity that is plotted on the X axis, and in such cases the dose-response curve is typically sigmoidal, with the steepest portion in the middle, indicating the half-maximal response. On the Y axis, the response is typically expressed as percentage of the maximal response observed, so that the quantity causing the half-maximal response is the quantity causing a 50% response rate, e.g. 50% inhibition ($IC_{50}$), or 50% efficacy ($EC_{50}$).

In one embodiment, the biological effect of the sample and the biological effect of the reference sample are determined in the same test particle.

In one embodiment, the biological activity is determined by determining one or more of the following parameters: time-dependent decrease of the amount of unchanged starting substrate, time-dependent increase of the amount(s) of one or more cleavage products resulting from proteolytic cleavage of the substrate, time-dependent decrease of the amount of a compound, e.g. a neurotransmitter, released from the test particle. The biological effect may be determined by using methods known in the art. For example, the amount of said substrate and said cleavage product may be determined in an immunoassay, e.g. in an ELISA assay capable discriminating between substrate and product. Moreover, release of said compound, e.g. neurotransmitter, may be determined by HPLC methods or by labeling said compound, e.g. neurotransmitter, with an appropriate isotope or fluorophore followed by measuring radioactivity or fluorescence in the test particle and/or the surrounding medium (Jones R G, Liu Y, Sesardic D. (2009) J Immunol Methods. 343 21-7).

In the context of the present invention, the term "membrane" refers to a layer that separates the outside of a test particle from the inside, where such layer is permissible, under appropriate conditions, for the clostridial neurotoxin, or components thereof. Such a membrane may be in the form of a lipid bilayer, e.g. as in naturally occurring cellular structures, or as in artificially generated structures, such as liposomal structures. Accordingly and as explained hereinabove, the lipid bilayer may be assembled de novo from its components, e.g. phospholipids, gangliosides and receptors, or may be obtained from a cell, e.g. an animal cell, particularly an animal cell derived from the CNS system, by preparation methods known in the art. In addition, it is conceivable that cell derived membranous particles be used in the methods of the present invention and be supplemented e.g. by particular phospholipids or polypeptides. Moreover, in certain cases it may be necessary to treat said particles prior to their use with proteases in order to remove unwanted proteins.

In the context of the present invention, the term "one or more receptors for said clostridial neurotoxin capable of mediating transfer of said clostridial neurotoxin to said reaction volume" refers to the receptors mediating cellular uptake of clostridial neurotoxin found in neuronal tissues susceptible for clostridial neurotoxin inhibition. Known receptors used by neurotoxins in the natural context are either glycolipids (e.g. Couesnon et al. Cell Microbiol. 2008 Feb.;10(2):375-87. 2007 Sep. 28.) or transmembrane proteins (for example, human SV2 for botulinum neurotoxin serotype A, or synaptotagmins I and II for botulinum neurotoxin serotype B), or both (e.g. Rummel et al., Proc Natl Acad Sci USA. 2007 Jan. 2;104(1):359-64 and Dong et al., Science. 2006 Apr. 28;312 (5773):592-6). However, even though naturally occurring receptors are preferred, the term "receptor", as used herein above refers to any membrane resident capable of mediating uptake into the lumen of the test particle. Hence, according to the teaching of the present invention, a phospholipid or a sugar or a polypeptide can be used as a receptor, as long as it is associated with the outer leaflet of the lipid bilayer and capable of mediating uptake of the neurotoxin into the lumen of the particle. Accordingly, the present invention's teaching extends to methods employing e.g. GPI-anchored receptor fragments, i.e. GPI-anchored molecules comprising the neurotoxin binding site of a naturally occurring receptor such as SV2. In particular cases, e.g. if the test particle of the present invention is assembled de novo, it may be advantageous to replace receptor molecules having multiple membrane spanning domains with GPI-anchored analogs thereof.

In the context of the present invention, the term "mediating transfer to said reaction volume" refers to the crossing of the light chain of the clostridial neurotoxin into the lumen of said test particle.

The inventors observe that the method of the present invention is very sensitive if the receptor density on de novo assembled test particles is particularly high. Surprisingly, this effect is also observed with cell derived test particles supplemented with additional receptor molecules. Accordingly, it is envisaged by the inventors to optimize the test particles by adding receptor molecules up to the point of optimal sensitivity.

In the context of the present invention, the term "substrate for the proteolytic activity of said clostridial neurotoxin" refers to any intracellular target for such clostridial neurotoxin (for example, human SNAP25 for botulinum neurotoxin serotype A, C and E, or Synaptobrevin for botulinum neurotoxin serotype B and F, and tetanus toxin). Such targets are proteins, which are involved in the formation of a functional SNARE complex. In one embodiment, such substrate is inactivated by interaction with the neurotoxin, in another embodiment, such substrate is inactivated by proteolytic cleavage.

The substrate of the present invention's method may be a naturally occurring substrate such as the full length SNAP-25 polypeptide or a derivative thereof. The term "derivative" refers for example to modified polypeptide substrates with N-terminal, C-terminal and/or internal truncations or additions, and to modified polypeptides comprising one or more amino acid additions, substitutions and/or deletions. Said polypeptide substrate may be of human origin or may have at least 50%, at least 60%, at least 70%, at least 80%, at least 90% or at least 95% sequence identity to the human polypeptide sequence.

In a certain aspect of the present invention, said substrate is labeled with one or more labels. The label may be for example a fluorescent label or a mixture of different fluorescent labels or any other detectable tag, including e.g. radioactive labels, DNA/RNA labels, Peptide or protein labels (GST, MBP, NusA, Ubiquitin etc. . . . ), enzyme labels (AP, HRP, Luciferase etc. . . . ) or physical labels such as non-radioactive isotopes.

In one embodiment of the method according to the first aspect of the invention, said method further comprises after step (a) the step of:
 (aa) adjusting the medium surrounding the test particle by decreasing the pH value.

The term "decreasing the pH value" as used herein means lowering the pH from pH 7.4 to a pH value below 6.5, particularly below pH 6, more particularly below pH 5 and more particularly between 4 and 5, and most particularly to about 4.5. Conditions that emulate the pH and redox gradient across endosomes, for example pH 5.3 on the cis-compartment containing BoNT and pH 7.0 on the trans-compartment supplemented for example with the membrane nonpermeable reductant Tris-(2-carboxyethyl) phosphine (TCEP) support channel activity. Without these pH and redox gradients across the membrane, no channel activity is recorded (Fischer A, Montal M., Proc Natl Acad Sci USA. 2007 Jun. 19;104(25): 10447-52). In a particular embodiment, such adjustment is performed in order to allow said transfer, i.e. the translocation of the light chain of the clostridial neurotoxin across the membrane into the lumen, i.e. the reaction volume of the test particle.

In a further embodiment of the method according to the first aspect of the invention, said method further comprises after step (a) the step of:
 (ab) adjusting the reaction volume in the test particle by decreasing the pH value; and/or
 (ac) adjusting the reaction volume in the test particle by increasing the reducing potential.

In a particular embodiment, such adjustment(s) is/are performed in order to allow to allow said proteolytic activity, i.e. the cleavage of the substrate by the light chain of the clostridial neurotoxin in the lumen, i.e. the reaction volume of the test particle.

In a further embodiment of the method according to the first aspect of the invention, step (b) comprises the step of:
 (ba) determining binding of the clostridial neurotoxin to the one or more receptors.

In particular embodiments, binding is determined by using binding molecules, such as antibodies, directed against the clostridial neurotoxin (i.e. direct determination of the amount of bound clostridial neurotoxin), or by using binding molecules, such as antibodies, directed against a receptor for the clostridial neurotoxin (i.e. indirect determination of the amount of bound clostridial neurotoxin by determining the amount of free, i.e. unbound receptors). In particular embodiments, the test particle/clostridial neurotoxin-complexes are first isolated, e.g. by centrifugation, and then washed in order to remove unbound clostridial neurotoxin. Subsequently, the amount of neurotoxin, which is bound to washed test particles, is determined e.g. in an immunoassay (e.g. ELISA, Western Blot).

In a further embodiment of the method according to the first aspect of the invention, step (b) comprises the step of:
 (ba) determining proteolysis of said substrate.

In particular embodiments, proteolysis is determined by ELISA or SNAPtide® methods. ELISA methods can be employed that use antibodies directed against either the uncleaved substrate or one or more of the cleavage products (see, for example, Ekong et al., Microbiology 1997; 143: 3337-47). The term "SNAPtide® methods" as used herein refers to an assay format which is based on the fluorometric measurement of botulinum toxin activity by providing fluorescently-labeled SNAP25-based substrates containing the native cleavage site for botulinum neurotoxin of serotype A (SNAPtide®), or of serotype E (SNAP Etide®). SNAPtide® and SNAP Etide® assays are available e.g. from List Biological Laboratories, Inc.

In certain embodiments of the methods of the present invention, the test particle is a test particle obtainable from a cell, in particular a non-cellular test particle, such as subcellular membrane fragments or erythrocyte ghosts which naturally or artificially contain appropriate receptors for the analyte.

In particular such embodiments, the non-cellular test particle is a synaptosome. In certain such embodiments, the synaptosome is derived from a mammalian brain e.g. a rat or mouse brain, or a brain from a transgenic animal expressing one or more human SNARE proteins.

In another embodiment, said non-cellular test particle is an artificially generated particle. The artificially generated particle may for example be a liposome. Such particle may be assembled essentially as described in: Liposome Drug Delivery Systems, G. V. Betageri, S. A. Jenkins, D. L. Parsons (1993). In short the test particle comprises
 a) a membrane e.g., a spherical phospholipid bilayer, enclosing an inner reaction volume.
 b) an inner reaction volume containing an adequate buffer system, e.g. 50 mM HEPES/20 μM ZnCl$_2$ pH 7.0 a reducing agent, e.g. 5 mM Dithiothreitol a proteolysis substrate for the clostridial neurotoxin c) structures targeting the receptor binding sites e.g., the receptors of clostridial neurotoxin Type A, i.e. the synaptic vesicle protein 2 (SV2) and the ganglioside GT1b. In one embodiment, these receptors are integrated into the membrane of the test particle exposing their targeting structures to the outer surface of the test particle.

In certain embodiments of the present invention, the clostridial neurotoxin referred to herein is a neurotoxin of *C. botulinum* and is of serotype A, B, C1, D, E, F or G or is a biologically active derivative thereof, wherein said derivative may be a genetically modified neurotoxin such as a mutant comprising a deletion of one or more amino acids, an addition of one or more amino acids and/or a substitution of one or more amino acids. Preferably, said deleted or added amino acids are consecutive amino acids. According to the teaching of the present invention, any number of amino acids may be added or deleted, as long as the neurotoxin is biologically active. For example, 1, 2, 3, 4, 5, up to 10, up to 15, up to 25, up to 50, up to 100, up to 200, up to 400, up to 500 amino acids or even more amino acids may be added or deleted. In certain aspects, the present invention refers to neurotoxins, with an addition of more than 500 amino acids, such as for example up to 600 or up to 800 additional amino acids, or even more additional amino acids. Accordingly, a derivative of the neurotoxin may be a biologically active fragment of a naturally occurring neurotoxin. This neurotoxin fragment may contain an N-terminal, C-terminal and/or one or more internal deletion(s). "Biologically active", as used in this context, means, said derivative is taken up into the nerve cell and is capable of denervating said nerve from the muscle or gland, to which it is connected. Moreover, said clostridial neurotoxin may be associated with complexing proteins or may be free of complexing proteins (see below).

In particular embodiments, the clostridial neurotoxin is of serotype A or E, and/or is a biologically active derivative thereof.

In the context of the present invention, the term "botulinum neurotoxin" refers to neurotoxins obtainable from *Clostridium botulinum*. Currently, seven serologically distinct types, designated serotypes A, B, C1, D, E, F and G, are known, including certain subtypes (e.g. A1, A2, and A3). In *Clostridium botulinum*, these neurotoxins are formed as protein complexes comprising a neurotoxic component and at least another non-toxic protein. Thus, the term "botulinum neurotoxin serotype A", as used herein, refers to the botulinum neurotoxin complex, such as the 450 kDa and the 900 kDa complexes which are e.g. obtainable from cultures of *Clostridium botulinum*. Preparations comprising such complexes are commercially available, e.g. from Ipsen Ltd. (Dysport®) or Allergan Inc. (Botox®).

Moreover, the term botulinum neurotoxin also refers to botulinum neurotoxin which is free of complexing proteins and which has a molecular weight of approximately 150 kDa. Thus, in particular embodiments, the clostridial neurotoxin is an isolated neurotoxic component of botulinum neurotoxin, particularly of botulinum neurotoxin of serotype A or E. In the context of the present invention, the term "isolated neurotoxic component of botulinum neurotoxin serotype . . . " refers to the neurotoxic component of the corresponding botulinum neurotoxin serotype complex free of complexing proteins. This neurotoxic component is a two-chain polypeptide with a 100 kDa heavy chain joined by a disulfide bond to a 50 kDa light chain. The heavy chain is responsible for entry into the neuronal cell, while the light chain comprises an endopeptidase activity responsible for cleaving one or more proteins that is/are part of the so-called SNARE-complex involved in the process resulting in the release of neurotransmitter into the synaptic cleft. A high purity neurotoxic component of the neurotoxin of *C. botulinum* of serotype A, free of any other botulinum protein, is e.g. available from Merz Pharmaceuticals GmbH, Frankfurt (Xeomin®).

The term "other isolated fragment of any said botulinum neurotoxin . . . , where such fragment has neurotoxic activity" refers to a neurotoxin complex that lacks certain of the non-toxic proteins of a botulinum neurotoxin as defined above, or certain parts of the neurotoxic component as defined above comprised therein, while maintaining the neurotoxic activity. Correspondingly, the term "other isolated fragment of any said . . . neurotoxic component, where such fragment has neurotoxic activity" refers to a neurotoxin component that lacks certain certain parts of the neurotoxic component of a botulinum neurotoxin as defined above, while maintaining the neurotoxic activity. Methods for making or identifying such fragments, and methods for identifying whether such fragments maintain neurotoxic activity, are well known to anyone of ordinary skill in the art.

In the context of the present invention, the term "derivative" and the term "variant or synthethic analogue" refer to a neurotoxin complex or neurotoxic component that is a chemically, enzymatically or genetically modified derivative of a neurotoxin as defined herein, including chemically or genetically modified neurotoxin from *C. botulinum*. A chemically modified derivative may be one that is modified by pyruvation, phosphorylation, sulfatation, lipidation, pegylation, glycosylation and/or the chemical addition of an amino acid or a polypeptide comprising between 2 and about 100 amino acids . An enzymatically modified derivative is one that is modified by the activity of enzymes, such as endo- or exoproteolytic enzymes. As pointed out above, a genetically modified derivative is one that has been modified by deletion or substitution of one or more amino acids contained in, or by addition of one or more amino acids (including polypeptides comprising between 2 and about 100 amino acids) to, the proteins of said neurotoxin or a neurotoxic component thereof. Methods for making such chemically or genetically modified derivatives, and methods for identifying whether such derivatives maintain neurotoxic activity, are well known to anyone of ordinary skill in the art.

In a particular embodiment, said clostridial neurotoxin is selected from the group of botulinum neurotoxin serotype A or E, the isolated neurotoxic component of botulinum neurotoxin serotype A or E, an isolated fragment of botulinum neurotoxin serotype A or E, or of the neurotoxic component of botulinum neurotoxin serotype A or E, where such fragment has neurotoxic activity, and any variant or synthetic analogue of botulinum neurotoxin serotype A, or E, respectively, or of the neurotoxic component thereof, where such variant or analogue has neurotoxic activity. The term "fragment" relates to a neurotoxin lacking 1, 2, 3, 4, 5, up to 10, up to 15, up to 25, up to 50, up to 100, up to 200, up to 400, up to 500 amino acids or even more amino acids. Preferably, said amino acids are consecutive amino acids.

Particularly, said clostridial neurotoxin is the neurotoxin of *C. botulinum* of serotype A, or is the isolated neurotoxic component of botulinum neurotoxin of serotype A, which is available from Merz Pharmaceuticals GmbH, Frankfurt (Xeomin®).

In certain embodiments of the first aspect of the present invention, said clostridial neurotoxin preparation is for pharmaceutical and/or aesthetic use.

In certain embodiments of the present invention, the clostridial neurotoxin in the clostridial neurotoxin preparation is produced in a fermentation process.

In particular embodiments the clostridial neurotoxin preparation is produced by a fermentation process using *Clostridium botulinum* strains. Methods for the fermentation process using *Clostridium botulinum* strains are well known in the art (see, for example, Siegel and Metzger, Appl. Environ. Microbiol. 38 (1979) 606-611; Siegel and Metzger, Appl. Environ. Microbiol. 40 (1980) 1023-1026).

In particular embodiments, the clostridial neurotoxin preparation is produced in heterologous cells, i.e. it is produced recombinantly by expressing nucleic acid sequences encoding a neurotoxin in an appropriate host cells. Methods for the recombinant expression of clostridial neurotoxin are well known in the art (see, for example, WO 2006/076902 or EP 1 206 554). An example of a heterologous cell is *E. coli*.

In certain embodiments of the present invention, the clostridial neurotoxin in said clostridial neurotoxin preparation and the reference clostridial neurotoxin belong to the same serotype.

In particular embodiments, the clostridial neurotoxin in said clostridial neurotoxin preparation and the reference clostridial neurotoxin are identical.

In this context, the terms "belong to the same serotype" and "identical" refer to the nature of the active neurotoxic agent present in the clostridial neurotoxin preparation and the reference clostridial neurotoxin. For example, when the clostridial neurotoxin preparation contains the isolated neurotoxic component (i.e. without any complexing proteins) of botulinum neurotoxin serotype A, and the reference clostridial neurotoxin is botulinum neurotoxin serotype A (i.e. the full complex), the clostridial neurotoxin in said clostridial neurotoxin preparation and the reference clostridial neurotoxin belong to the same serotype, but are not identical. When the clostridial neurotoxin preparation contains the isolated neurotoxic component (i.e. without any complexing proteins) of botulinum neurotoxin serotype A, and the reference clostridial neurotoxin is the isolated neurotoxic component of botulinum neurotoxin serotype A as well, the clostridial neurotoxin in said clostridial neurotoxin preparation and the reference clostridial neurotoxin are identical (even though the clostridial neurotoxin preparation and the preparation containing the reference clostridial neurotoxin may differ in the amount and concentration of the respective neurotoxin and/or the presence of additional ingredients such as buffers, excipients etc.)

In particular embodiments, the clostridial neurotoxin is of serotype A, and the one or more receptors are taken from the list of: SV2, a ganglioside receptor, and a biologically active derivative of SV2 or a ganglioside receptor.

In particular such embodiments, the ganglioside receptor is taken from the list of GT1b (see Rummel et al., Molecular Microbiology 2004; 51: 631-43) and GD1b.

In particular embodiments, the substrate is SNAP-25 or a biologically active variant thereof.

EXAMPLES

Example 1

Determination of Biological Effects in Rat Brain Synaptosomes

A preparation of rat brain synaptosomes is obtained as described in the literature from a Percoll gradient after homogenization of rat brain (see Rummel et al., Molecular Microbiology 2004; 51: 631-43). The synaptosomes are diluted in physiological buffer (e.g. 140 mM NaCl, 5 mM KCl, 1 mM $MgCl_2$, 1 mM $CaCl_2$, 20 mM Hepes, 10 mM glucose, 0.5% BSA, pH 7.4). The amount of synaptosomes being present is determined by determining the total amount of synaptosomal proteins. For all experiments, a fixed concentration of total synaptosomal proteins, e.g. 10 mg/ml, is being used.

A fixed amount of different dilutions from a dilution series of a reference botulinum neurotoxin serotype A with known biological activity (expressed as mouse units) is added to the synaptosome preparation. After incubation for about 2 h at about 0° C., the synaptosomes are repeatedly washed using physiological buffer and centrifugation, in order to remove unbound neurotoxin. Thereafter, the pH of the solution to pH 4.5 by adding, for example, 1 M HCl. Incubation is continued for about 30 min. Synaptosomes are lysed using, for example, Triton X-100 (see Sahyoun et al., J. Biol. Chem. 1989; 264: 1062-1067), and the amounts of SNAP25 and/or its cleavage products are determined in an ELISA assay as described (Ekong et al., Microbiology 1997; 143: 3337-47). During work-up of the synaptosomes, a botulinum neurotoxin inhibitors, such as described, for example, by Boldt et al., Chem. Commun., 2006, 3063-3065, can be added to terminate the proteolytic activity of the neurotoxin.

The same experiment is repeated with a dilution series of the clostridium neurotoxin preparation in otherwise identical fashion. The amount of clostridium neurotoxin preparation necessary to achieve $EC_{50}$ (i.e. the half-maximal cleavage of the SNAP25 substrate) can then be correlated to the corresponding amount of reference botulinum neurotoxin serotype A with known biological activity.

Example 2

Determination of Biological Effects in Artificial Vesicles

Liposomes are formed from phospholipids, such as phosphatidylethanolamine, phosphatidylcholine, or mixtures thereof, as described in the literature, in the presence of recombinant SV2, GT1b and/or GD1b, and SNAPtide® (o-Abz/Dnp) or SNAPtide® (FITC/DABCYL) (List Biological Laboratories, Inc., Product Nos. 520 and 521, respectively). o-Abz/Dnp). The resulting liposomes are repeatedly washed in order to remove the excess of reactants not incorporated into the liposomes. The amount of SV2 integrated into the membranes can be determined by using antibodies directed against SV2 (Santa Cruz Biotechnology, Inc.).

A fixed amount of different dilutions from a dilution series of a reference botulinum neurotoxin serotype A with known biological activity (expressed as mouse units) is added to the liposome preparation. After incubation for about 2 h at about 0° C., the liposomes are repeatedly washed using physiological buffer and centrifugation, in order to remove unbound neurotoxin. Thereafter, the pH of the solution to pH 4.5 by adding, for example, 1 M HCl. Incubation is continued for about 30 min, and the increase in fluorescence intensity is being determined (see instruction manual for the SNAPtide® assay), which is directly proportional to the amount of cleavage that is occurring. Alternatively, the cleavage reaction can directly be observed inside the test particle by using fluorescence correlation spectroscopy (see, for example, Brock and Jovin (1998). Fluorescence correlation microscopy (FCM) - fluorescence correlation spectroscopy (FCS) taken into the cell. Cell. Mol. Biol. 44, 847-856).

The same experiment is repeated with a dilution series of the clostridium neurotoxin preparation in otherwise identical fashion. The amount of clostridium neurotoxin preparation necessary to achieve $EC_{50}$ (i.e. the half-maximal cleavage of the SNAPtide® substrate) can then be correlated to the corresponding amount of reference botulinum neurotoxin serotype A with known biological activity.

The invention claimed is:

1. An in vitro method for determining the biological activity of a preparation of a clostridial neurotoxin, comprising the steps of:
    (a) contacting at least one test particle with a sample of the clostridial neurotoxin preparation;
    (b) measuring one or more parameters selected from time-dependent decrease of an amount of unchanged starting substrate within the test particle, time-dependent increase of an amount of one or more cleavage products resulting from proteolytic cleavage of a substrate within the test particle, time-dependent decrease of an amount of a compound released from the test particle; and
    (c) comparing the measurement of the parameter in step (b) of the sample of the clostridial neurotoxin preparation with the measurement of the parameter in step (b) of a reference sample, thereby determining the amount of the biological activity of the clostridial neurotoxin in the preparation;
wherein the at least one test particle comprises at least a membrane enclosing a reaction volume, wherein the membrane carries one or more clostridial neurotoxin receptors which bind the clostridial neurotoxin and mediate internalization of the clostridial neurotoxin into the reaction volume, and wherein the reaction volume comprises a substrate for clostridial neurotoxin which is proteolytically cleaved by the clostridial neurotoxin in the reaction volume of the test particle.

2. The method of claim 1, further comprising after step (a), a step of:
    (aa) adjusting the medium surrounding said teat particle by decreasing the pH value.

3. The method of claim 1, further comprising after step (a), a step of:
    (ab) adjusting the reaction volume in the test particle by decreasing the pH value; and/or
    (ac) adjusting the reaction volume in the test particle by increasing the reducing potential.

4. The method of claim 1, wherein step (b) comprises a step of:
    (ba) determining binding of the clostridial neurotoxin to the one or more receptors.

5. The method of claim 1, wherein the proteolytic cleavage of a substrate is determined by Enzyme-Linked Immunosorbent Assay (ELISA) or fluorometric measurement of botulinum toxin activity on a fluorescently labeled synaptosomal-associated protein 25 kDa (SNAP-25)-based substrate containing the native cleavage site for botulinum neurotoxin of serotype A or serotype E.

6. The method of claim 1, wherein the test particle is a non-cellular test particle.

7. The method of claim 6, wherein the non-cellular test particle is a synaptosome.

8. The method of claim 6, wherein the non-cellular test particle is an artificially generated particle.

9. The method of claim 1, wherein the clostridial neurotoxin is a *Clostridium botulinum* neurotoxin of serotype A, B, C1, D, E, F or G, or is a biologically active derivative thereof.

10. The method of claim 9, wherein the clostridial neurotoxin of serotype A or E, or is a biologically active derivative thereof.

11. The method of claim 10, wherein the clostridial neurotoxin is of serotype A, and wherein one or more receptors on the membrane are selected from synaptic vesicle protein 2 (SV2), a ganglioside receptor, a biologically active derivative of SV2, and combinations thereof.

12. The method of claim 11, wherein the ganglioside receptor is selected from GT1b and GD1b.

13. The method claim 1, wherein the substrate is synaptosomal-associated protein 25 kDa (SNAP-25) or a biologically active variant thereof.

14. A kit for determining the biological activity of a preparation of a clostridial neurotoxin comprising:
    (a) at least one test particle comprising at least a membrane enclosing a reaction volume, wherein the membrane carries one or more clostridial neurotoxin receptors which bind the clostridial neurotoxin and mediate internalization of the clostridial neurotoxin into the reaction volume, and wherein the reaction volume comprises a substrate for clostridial neurotoxin which is proteolytically cleaved by the clostridial neurotoxin in the reaction volume of the test particle;
    (b) one or more reagents for determining binding of the clostridial neurotoxin to the one or more receptors; and/or
    (c) one or more reagents for determining proteolytic cleavage of the substrate.

* * * * *